United States Patent
Belanger et al.

(10) Patent No.: US 8,449,769 B2
(45) Date of Patent: May 28, 2013

(54) DEVICE, APPARATUS AND METHOD FOR PERFORMING SEPARATIONS

(75) Inventors: Jonathan Belanger, Whitinsville, MA (US); Micah Inglis Watt, Attleboro, MA (US); Stephen J. Shiner, Holden, MA (US)

(73) Assignee: Waters Technologies Corporation, Milford, MA (US)

( * ) Notice: Subject to any disclaimer, the term of this patent is extended or adjusted under 35 U.S.C. 154(b) by 545 days.

(21) Appl. No.: 12/526,286

(22) PCT Filed: Feb. 19, 2008

(86) PCT No.: PCT/US2008/054237
§ 371 (c)(1),
(2), (4) Date: Sep. 30, 2010

(87) PCT Pub. No.: WO2008/121453
PCT Pub. Date: Oct. 9, 2008

(65) Prior Publication Data
US 2011/0259827 A1    Oct. 27, 2011

Related U.S. Application Data

(60) Provisional application No. 60/891,091, filed on Feb. 22, 2007, provisional application No. 61/025,416, filed on Feb. 1, 2008.

(51) Int. Cl.
*B01D 15/08* (2006.01)
(52) U.S. Cl.
USPC ...................................... 210/198.2; 210/656
(58) Field of Classification Search
USPC ..... 210/635, 656, 198.2; 96/101, 106; 422/70
See application file for complete search history.

(56) References Cited

U.S. PATENT DOCUMENTS

| | | | | |
|---|---|---|---|---|
| 4,587,014 | A | * | 5/1986 | America ................... 210/198.2 |
| 4,861,473 | A | | 8/1989 | Shackelford et al. |
| 4,876,005 | A | * | 10/1989 | America ................... 210/198.2 |
| 7,101,477 | B1 | | 9/2006 | Willis et al. |
| 2005/0011835 | A1 | | 1/2005 | Henderson et al. |
| 2006/0186029 | A1 | | 8/2006 | Granger et al. |
| 2007/0090035 | A1 | | 4/2007 | Rahn et al. |
| 2008/0257835 | A1 | * | 10/2008 | Benevides et al. ........... 210/767 |
| 2011/0259827 | A1 | * | 10/2011 | Belanger et al. ............. 210/656 |

FOREIGN PATENT DOCUMENTS

| | | |
|---|---|---|
| EP | 0328146 | 8/1989 |
| WO | 2005087340 | 9/2005 |
| WO | 2006023524 | 3/2006 |
| WO | 2006055675 | 5/2006 |
| WO | WO 2006/055675 * | 5/2006 |

OTHER PUBLICATIONS

European search report for EP Application No. 08780433.2, cf Form 1507, dated Nov. 25, 2011, 8 pages.
PCT International Search Report for PCT Application No. PCT/Us08/54237, Form PCT/ISA/220 + 210, dated Sep. 16, 2008, 3 pages.
PCT International Written Opinion Report or PCT Application No. PCT/Us08/54237, Form PCT/ISA/237, dated Sep. 8, 2008, 6 pages.

* cited by examiner

*Primary Examiner* — Ernest G Therkorn
(74) *Attorney, Agent, or Firm* — Waters Technologies Corp

(57) ABSTRACT

Embodiment of the present invention feature a device having a body, a separation media and a frit element. The exterior surface of the body has a first attachment means positioned radially about at least one of the media chamber and the frit section to form a compact assembly.

31 Claims, 5 Drawing Sheets

DEVICE, APPARATUS AND METHOD FOR PERFORMING SEPARATIONS

CROSS REFERENCE TO RELATED APPLICATIONS

This application is the National Stage of International Application No. PCT/US2008/54237, filed Feb. 19, 2008, which claims priority to and benefit of U.S. Provisional Patent Application Ser. No. 60/891,091, filed Feb. 22, 2007 and U.S. Provisional Patent Application Ser. No. 61/025,416, filed Feb. 1, 2008. The entire contents of these applications are incorporated herein by reference.

STATEMENT REGARDING FEDERALLY SPONSORED RESEARCH AND DEVELOPMENT

The present invention was not made with Federal funding.

FIELD OF THE INVENTION

The present invention relates to devices, methods and apparatus for performing separations, and, in particular, separations performed by chromatography for analytical purposes.

BACKGROUND OF THE INVENTION

The present invention relates to devices, methods and apparatus for performing chemical separations, and, in particular, for performing chromatography. The term "chromatography" refers to the separation of compounds based on differences in affinity or absorbance. In chromatography, compounds are held in a solution of a gas, liquid or supercritical fluid. The solution in which the compound is dissolved is known as the "solvent". The dissolved compounds exhibit differences in absorbance or affinity to a media that is not dissolved in the solvent. This media is held in place, stationary to the flow of a solution holding the dissolved compounds. This media is commonly a solid phase material.

Chromatography is a common research tool and can be used to process samples for analysis by various detection techniques. Chromatography is used to grossly separate many compounds from a sample, as an extraction technique. Chromatography can also be utilized as a fine separation technique in which subtle changes in molecular structure and function alter the affinity of the compounds to an immobilized media. Closely related compounds, for example drugs and drug metabolites, can be effectively separated.

Chromatography is performed in open systems or closed systems. In open systems chromatography is performed without significant pressure differentials. Examples of devices used in an open type system are well-like devices, such as ninety-six well extraction plates.

An example of a closed system is high performance or high pressure liquid chromatography (HPLC). Closed chromatography is normally performed with columns and cartridges through which solutions are pumped under pressure. The columns and cartridges typically have a packing of an immobilized media, such as silica or polymeric particles, to which compounds adsorb. A sample is flowed through the media and compounds in the sample adsorb to the media. This paper will make no distinction between a column and cartridge, and will use the term "column" to mean column or cartridge unless specifically stated otherwise. Analytical columns are columns made with fine tolerances for effecting reproducible qualitative and quantitative separations of closely related compounds. Columns, and analytical columns, in particular, are expensive.

The initial flowing of sample onto the media is called "loading". Removing the potential compounds of interest is known as "eluting". Elution is often performed by changing the solvent composition. Preparing the media to receive the sample is known as "conditioning". Ensuring the prior sample is removed from the media, to allow a next sample to be loaded on the media is known as "washing".

The term "sample" will be used to denote any material that is received for processing. In clinical settings, a sample may comprise a biological fluid or tissue. The term "analyte" will be used to mean a composition of interest, potentially present in a sample. Samples and solvents may contain particulates, globules and other materials that are not of analytical or diagnostic interest. For simplicity, this paper will refer to all such particulates, globules and materials as particulates. These particulates may accumulate and reduce flow in columns such that the column no longer is useful.

Columns are normally in fluid communication with a detector. As used in this paper, the term "detector" refers to a device that produces a signal in response to the presence or absence of a composition. A typical detector is in the nature of, by way of example, without limitation, mass spectrometers, optical sensors, such Raman detectors, light scattering detectors, fluorescent detectors, chemi-luminescent detectors, light absorbance detectors, light refraction detectors, electrochemical detectors, viscosity detectors, nuclear magnetic resonance detectors.

HPLC is normally performed at pressure of up to 5,000 pounds per square inch (psi). However, there is a desire to operate at pressures above 5,000 psi, including pressures in the extreme pressure region of 5,000 psi up to 15,000 psi. At such elevated pressures and with higher flow rates associated with such pressures, the size of columns and conduits to effect fluid communication between fluidic elements is generally reduced. With the smaller size, columns are more sensitive to particulates and pressure pulsation. As used herein, pressure pulsation refers to the changes in pressure associated with pump, valve and other mechanical inefficiencies and errors.

Guard columns are used to protect and extend the useful life of analytical columns. However, the use of guard columns to protect other columns, such as an analytical column, often entails substantial additional conduits and tubing. The additional tubing and conduits adds to the potential of leaks and contributes to band spreading due to the effects of the walls of the conduits and tubes, and decreases the responsiveness of the system to changes in fluids during elution process or washing processes.

Thus, there is a need for devices, methods and apparatus which function to protect a column and detector sensitive to the effects of particulates and pressure pulsations and ripples in a high pressure and extreme high-pressure environment.

SUMMARY OF THE INVENTION

Embodiments of the present invention feature a device, apparatus and method of separating one or more compounds of interest from each other or from undesired compounds or particulates. One embodiment of the device has a body, a separation media and a frit element.

The body has an interior body surface, an exterior body surface, a first body opening at a first body end and a second body opening at a second body end. The first body opening and the second body opening define a boundary between the interior body surface and the exterior body surface. The interior body surface has at least one wall creating a passage in the body. The passage has at least one frit section and a media chamber proximal to the first opening and a manifold section proximal to the second opening. The frit section is for holding a frit element. The media chamber is for holding a separation media. The manifold section is for receiving or discharging fluid from the frit section. The exterior body surface has a first union means and at least one of the exterior body surface and the interior body surface has a second union means. The first union means is towards the first opening for placing the media chamber in fluid communication with either a source of fluid or a fluid discharge conduit or a column or detector. The second union means is towards the second opening for placing the manifold section in communication with either a source of fluid or a fluid discharge conduit or a column or detector. The exterior surface has a first attachment means positioned radially about at least one of the media chamber and the frit section.

The separation media is held within the media chamber for effecting separations of compounds in solutions flowing therethrough. The frit element is held in the frit section for retaining the separation media. The body receives a first conduit attachment means and a second attachment means to place said passage in fluid communication with a solution to effect separation of one or more the compounds from other compounds in the solution or undesired particulates.

Preferably, the device comprises a first frit element received in the frit section and a second frit element. The second frit is received at or about the first end in a second frit section of the passage or about the exterior surface. For example, one embodiment features an exterior surface having a rim extending around the first opening for receiving a frit disc as a second frit element. Preferably, the rim has a planar rim surface and at least one rim ridge surrounding the first opening. The frit disc has a planar disc surface for receiving the rim ridge and sealing the frit disc upon compression against said rim.

Preferably, the device has a first union means fitted to the frit disc. The first union means is for attachment to a conduit for removing fluid from or placing fluid into the frit element, or to place into communication with a column or a detector.

One preferred first union means comprises a rod assembly and compression fitting. The rod assembly has tube section and a compression plate section. The tube section is in fluid communication with the frit disc. The plate section has a first planar surface for pressing in sealing relationship to the frit disc and a second surface for receiving a compression surface of a compression fitting. The compression fitting is received on said first attachment means of the body for compressing the plate section and frit disc against the rim.

Preferably, the compression fitting has a fitting interior surface and a fitting exterior surface, a first fitting opening and a second fitting opening. The fitting interior surface defines a tube channel between the first fitting opening and the second fitting opening. The tube channel has a narrow section, an expanded section and a compression surface. The compression surface is interposed between the narrow section and the expanded section. The expanded section and the attachment means of the body having cooperating threads to allow the compression surface to compress the plate section and frit disc on the rim with said tube section received in and extending from the tube channel.

Thus, the rod assembly is received in the compression fitting with the tube section in the tube channel and extending outwardly from the first fitting opening, and the plate section abutting the compression surface. Turning the compression fitting with respect to the body compresses the plate section, the frit disc and the rim of the body in sealing engagement. Preferably, at least one of, and even more preferably, both the body and the compression fitting have exterior surfaces that facilitate rotation such as knurled surfaces, wrench receiving notches and other turning surfaces. Preferably, the turning surfaces on the compression fitting are recessed and are proximal to the second opening. The recessed turning surfaces are preferably concealed by a tube compression assembly. The tube compression assembly is received on the tube section of the rod assembly to place the tube section in fluid communication with a detector, column or conduit.

Preferably, the tube compression assembly comprises a ferrule and a ferrule fitting. Thus, the ferrule and the ferrule fitting are received on the tube extending from the compression fitting. The ferrule fitting has a ferrule fitting interior surface, a ferrule fitting exterior surface, a ferrule fitting first opening and a ferrule fitting second opening. The ferrule fitting interior surface defining a ferrule fitting tube channel between the ferrule fitting first opening and the ferrule fitting second opening. The ferrule fitting tube channel has a ferrule fitting narrow section and a ferrule fitting expanded section. The ferrule fitting narrow section receives the tube section. The ferrule fitting expanded section receives the compression fitting turning surfaces to conceal such turning surfaces. Thus, the user is discouraged from separating the body from the compression fitting, potentially compromising the separation media contained therein.

Preferably, the ferrule fitting has a male end at the ferrule fitting second opening. And, preferably, the ferrule fitting has a ferrule fitting rim for receiving the ferrule to allow said ferrule to be compressed by a cooperating ferrule female fitting. The male end and the female ferrule fitting, preferably have cooperating threads.

Preferably, second body end has second end attachment means for affixing, in fluid communication, to an analytical column, detector or a conduit. For example, without limitation, second end attachment means comprise cooperating threads for receiving cooperating threads of a column, or a detector or conduit, or a further fitting including ferrule compression fittings and the like.

A further embodiment of the present invention comprises a method of separating compounds in a solution from each other or undesired components of the solution. The method comprises the step of providing a device having a body, a separation media, and a frit element as previously described, and flowing solutions through the device to separate compounds from each other or from particulates.

A further embodiment of the present invention comprises an apparatus. The apparatus has a device as previously described and one or more instruments selected from the group comprising a high performance chromatography pump, detector and column.

Thus, embodiments of the present invention feature a device, method and apparatus for separating one or more compounds from each other or from particulates. The device has small internal volumes and therefore does not contribute significantly to band spreading. The device is readily manufactured and conceals features that would potentially lead to undesirable opening of the separation media.

These and other features and advantages will be apparent to those skilled in the art upon reading the detailed description of the invention and viewing the drawings.

DETAILED DESCRIPTION OF THE INVENTION

Embodiments of the present invention will be described with respect to a column used to protect a analytical column, commonly referred to as a guard column with the understanding that such column can be used for performing chromatography without an analytical column. Indeed, such column can be used directly with analytical, diagnostic instruments, detectors and the like. The description that follows describes a preferred embodiment of the device, methods and apparatus of the present invention. Those skilled in the art will readily recognize that the present invention can be modified and altered to address specific needs without departing from the present teaching.

Figure 1:
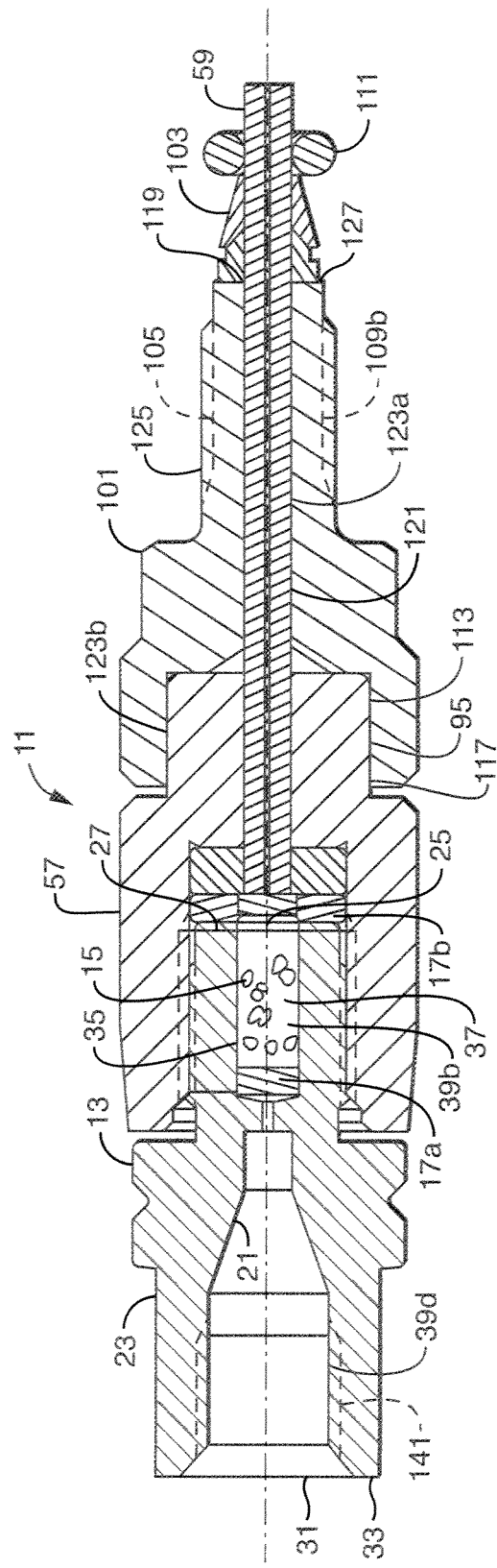
FIG. 1 depicts a cross-sectional view of a device embodying features of the present invention.

Turning now to FIG. 1, a device, generally designated by the numeral 11 is depicted in cross-section. The device is for separating one or more compounds of interest from each other or from undesired compounds or particulates. The device 11 has the following major components: a body 13, a separation media 15 and frit element 17a and 17b.

Figure 2:
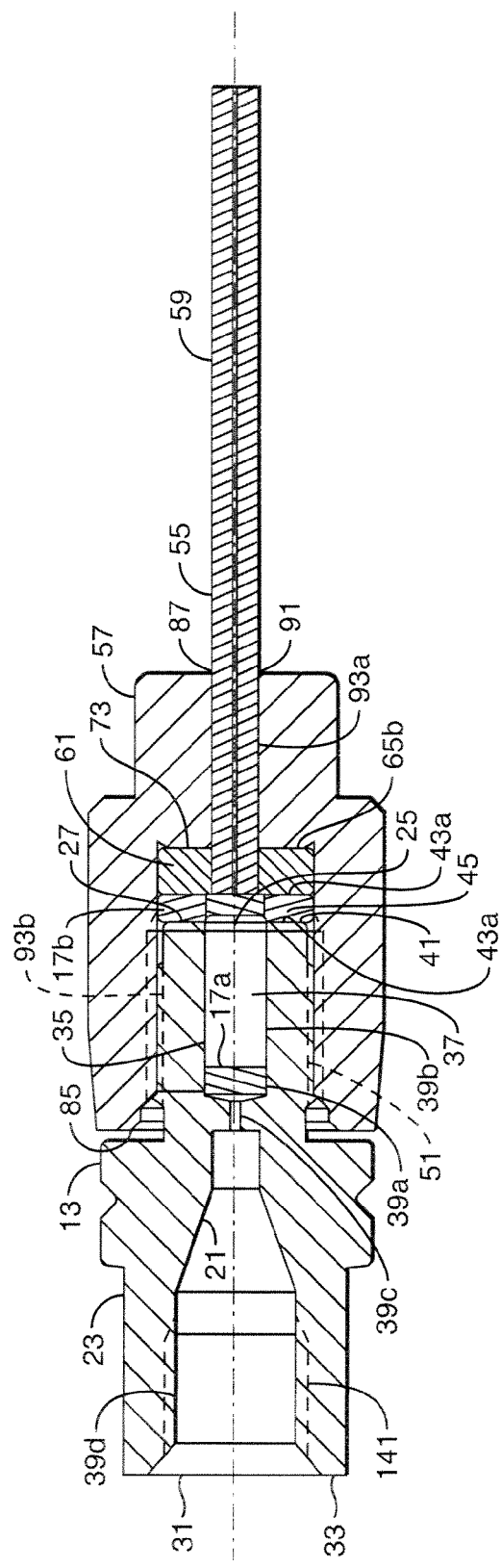
FIG. 2 depicts a cross-sectional view of a device embodying features of the present invention.

As best seen in FIG. 2, the body 13 has an interior body surface 21, an exterior body surface 23, a first body opening 25 at a first body end 27 and a second body opening 31 at a second body end 33. The first body opening 25 and the second body opening 31 define a boundary between the interior body surface 21 and the exterior body surface 23. The interior body surface 21 has at least one wall 35 creating a passage 37 in the body 13. The body 13, and all components of the device 11, unless otherwise indicated, is made of a substantially rigid material such as plastic and metal. A preferred metal is titanium, brass, and stainless steel. The body 13, for extreme high pressure applications is approximately 2.1 millimeters in diameter and 5 millimeters in length. The passage 37 is about 0.050 to 0.0005 inches in diameter at its narrowest.

The passage 37 has at least one frit section 39a and a media chamber 39b proximal to the first opening 25. And, the passage 37 has a manifold section 39c in fluid communication with the frit section 39a and a connection section 39d more proximal to the second opening 31.

The frit section 39a is for holding first frit element 17a. The media chamber 39b is for holding the separation media 15, which comprises a porous monolith, packed bed of particles, beads or other solid forms or fibers [not shown], known in the art. The separation media 15 is held within the media chamber 39b for effecting separations of compounds in solutions flowing therethrough. For guard column applications at extreme pressures, chamber 39a has a volume of 17 to 19 cubic mm. When packed with a bed of particles, the preferred particles are packed at similar extreme pressures. A preferred particle bed has particles having a mean diameter of 1.7 microns.

A first frit 17a is held in the frit section 39a for holding the packed bed of particles in the media chamber 39b. First frit 17a is porous filter disc made of a material such as titanium, plastic or stainless steel in a manner known in the art.

The manifold section 39c is for receiving from or discharging to the frit section 39a. The connection section 39d is constructed and arranged as a union means for receiving a fitting [not shown] to place the manifold section in fluid communication with a further conduit, instrument, or detector. Those skilled in the art will readily recognize that such union means can be formed as part of the exterior surface 23.

Figure 3A:
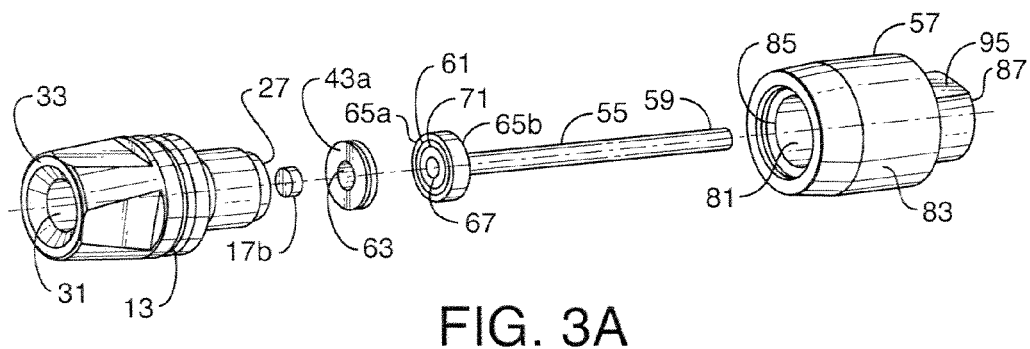
FIG. 3a depicts an exploded view of the device in FIG. 2.
Figure 3B:
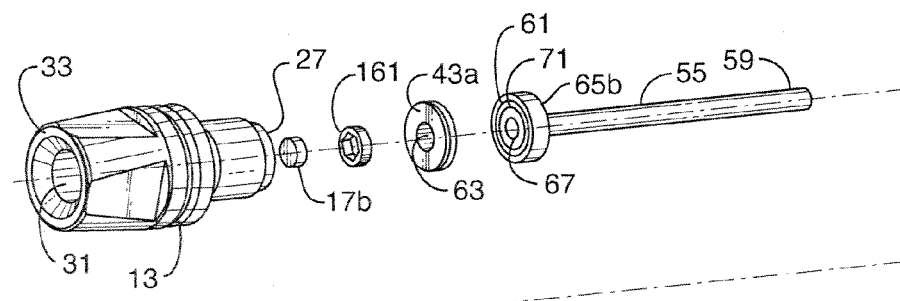
FIG. 3b depicts an exploded view of the device in FIG. 1 with a wiper and projecting frit.
Figure 3B:
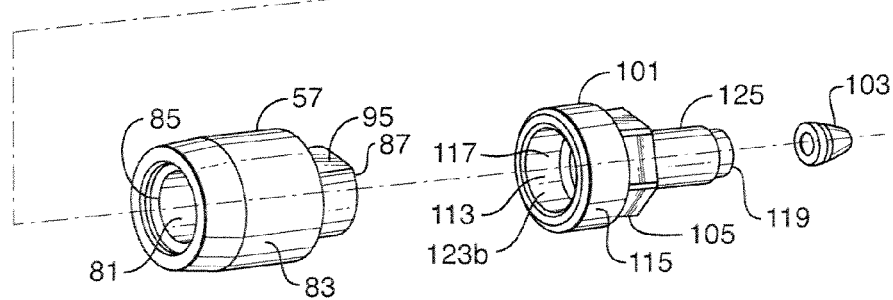
Figure 3C:
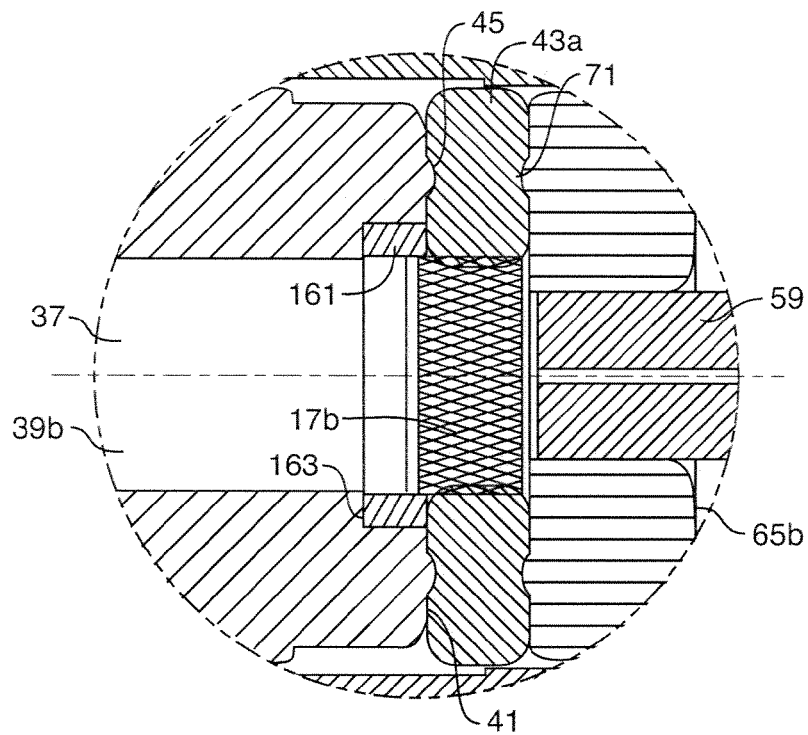
FIG. 3c depicts an detailed view of the device in FIG. 3b.

A second frit element comprising a second frit 17b and a frit sealing ring 43a is received at or about the first body end 27 in a second frit section of the passage [not shown] in the manner of the first frit 17a, or, as shown in FIGS. 2 and 3a, outside the first body 13 end surface 27, or a combination of a second frit section of the passage and projecting outside the passage surface 27 as shown in FIGS. 3b and 3c to be discussed in greater detail below.

Returning now to FIGS. 2 and 3a, second frit 17b, like first frit 17a, is a porous filter disc made of a material such as titanium, plastic or stainless steel. Second frit 17b is held in frit sealing ring opening 63 of frit sealing ring 43a.

Exterior surface 23 has a rim 41 extending around the first body opening 25. Rim 41 has a planar rim surface for receiving frit sealing ring 43a. Turning now to FIG. 2a, frit sealing ring 43a has a flat surface that mates with the flat surface of rim 41. At least one of the flat surface of rim 41 and the flat surface of frit sealing ring 43a has ridge. As depicted, in FIG. 2, the rim surface 41 has a ridge 45 surrounding the first opening 25. The frit sealing ring 43a receives the ridge 45 against the ring flat surface. The ridge 45 seals the frit sealing ring 43a upon compression against said rim 41.

Turning now to FIGS. 3b and 3c, such figures depict an embodiment in which the second frit 17b, is placed into the chamber 39b which would be occupied by particles of other separation media. Preferably, a compression element, such as a sleeve [not shown], frit sealing ring 43a, a wiper element 161, to be discussed in greater detail later, or, as described herein, second frit 17b is compelled into the media held in chamber 39b to occupy approximately 0.1 to 5% of the total area occupied by particles not under pressure. More preferably, the compression element such as second frit 17b is forced into the at-rest particles to occupy approximately 2% of the volume. Compression presses the particles to form an interstitial volume fraction of approximately 0.38 to 0.35. And, preferably, compression presses the particles to form an interstitial volume fraction of approximately 0.365 to 0.375. These interstitial volume fractions represent a reduction of at-rest interstitial volume fraction of approximately 5 to 15%, and preferably of about 8 to 12%. The compressed particles have an optimal bed density to promote stability of the bed and avoid the formation of voids.

Thus, frit sealing ring 43a and second frit 17b are sized to allow second frit 17b to project outside the frit seal ring opening 63. The amount of projection can be changed by changing the thickness of the second frit 17b or the frit sealing ring 43a. The portion of the second frit 17b projecting outside the opening 63, as best seen in FIG. 3c, occupies a space of 2% of the volume of the particles that would occupy chamber 39b. For a chamber of approximately 18 cubic milimeters in volume and 2.1 mm in diameter, the amount of projection is approximately 0.051 to 0.330 mm.

Again referring to FIGS. 3b and 3c, a wiper 161 is received in a recess 163 in the passage 37 forming chamber 39b. The wiper 161 is a ring of resilient material such as plastic to provide radial compression of the packed material forming the bed and to facilitate the compression of the bed upon the pressing the second frit 17b into the chamber 39b. A preferred plastic is a fluoropolymer sold under the mark TEFLON® (Dupont). The second frit 17b is normally fitted to the first body 13 after the particles are loaded. The remainder of the structures of FIGS. 3b and 3c are as described with respect to FIG. 3a.

Turning now to FIG. 2, the body 13 is fitted to conduits, instruments and detectors by first union means comprising cooperating fittings, conduits or structures associated with instruments and detectors. First union means, as depicted, comprises the exterior body surface 23 and attachment surfaces 51 positioned radially about at least one of the media chamber 39b and the frit section 39a. Attachment surfaces comprise pins, cams and locking fittings known in the art, and as illustrated, a threaded section of the body 13.

Turning now to FIGS. 2 and 3, one first union means comprises a rod assembly 55 and compression fitting 57. The rod assembly is preferably made of rigid plastic, and metals such as brass, titanium and stainless steel. The rod assembly 55 has a tube section 59 and a compression plate section 61. The tube section 59 is in fluid communication via port 67 with the frit center opening 63 of second frit 17b.

The compression plate section 61 has a first plate surface 65a for pressing in sealing relationship against the corresponding planar surface of frit sealing ring 43a. Preferably, at least one of the plate surface 65a and the planar surface of the frit sealing ring 43a has a ridge for effecting a seal. As depicted in FIG. 3a, first plate surface 65a has a ridge 71 extending around the port 67. Upon compression the ridge 71 presses into and seals the frit sealing ring 43a against the plate section 61. The compression plate section 61 has a second plate surface 65b for receiving a compression surface 73 of compression fitting 57.

Compression fitting 57 has a fitting interior surface 81 and a fitting exterior surface 83, a first fitting opening 85 and a second fitting opening 87. As best seen in FIG. 2, the fitting interior surface 81 defines a tube channel 91 between the first fitting opening 85 and the second fitting opening 87.

Tube channel 91 has a narrow section 93a, an expanded section 93b and compression surface 73. The compression surface 73 is interposed between the narrow section 93a and the expanded section 93b. The expanded section 93b and the attachment surfaces 51 of the body 13 have cooperating threads to allow the compression surface 73 to compress the compression plate section 61 and frit sealing ring 43a on the rim 41 of the body 13. The tube section 59 is received in and extends from the tube channel 91.

Rotation of the compression fitting 57 with respect to the body 13 in one direction compresses the compression plate section 61, the frit sealing ring 43a and the rim 41 of the body 13 in sealing engagement. Rotation of the compression fitting 57 in the opposite direction causes decompression and loss of the sealing engagement. Preferably, at least one of, and even more preferably, both the body 13 and the compression fitting 57 have exterior surfaces that facilitate rotation such as knurled surfaces, wrench receiving notches and other turning surfaces. Such turning surfaces facilitate manufacture of the device 11.

Figure 4:
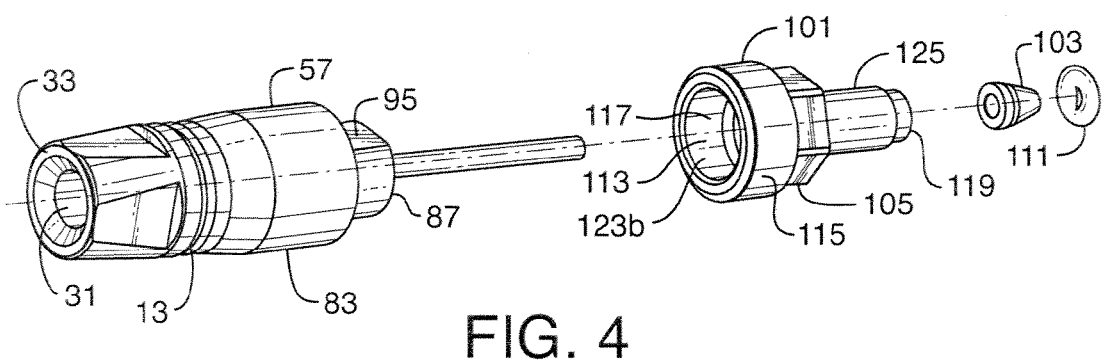
FIG. 4 depicts an exploded view of the device of FIG. 1.

However, it is desirable to maintain the sealing relationship of the compression plate section 61, the frit sealing ring 43a and the rim 41 of the body 13 after the device is packed with separation media 15. Disruption of the sealing relationship disturbs the separation media 15 making such media less effective. It is desirable in this regard to not allow or discourage rotation of the compression fitting 57 and the body 13 after the device 11 is made. As best seen in FIGS. 3 and 4, compression fitting 57 has an exterior surface 83 having turning surfaces 95 in the form of notches for receiving a wrench or similar tool [not shown]. The turning surfaces 95 are recessed and are proximal to the second opening 87.

Figure 5:
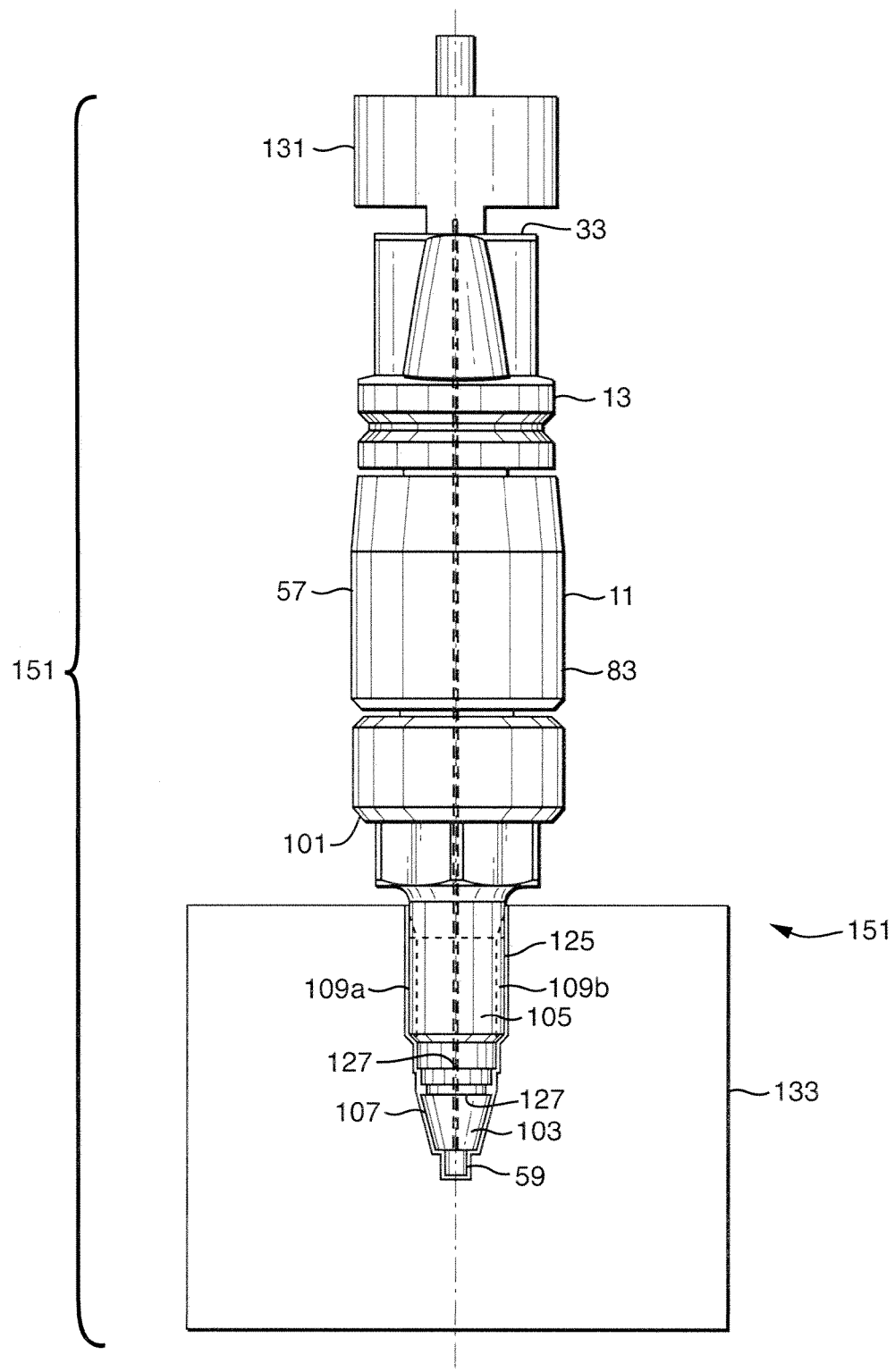
FIG. 5 depicts a view of the device of FIG. 1 in partial cross-section with a further column, conduit, or instrument.

The turning surfaces 95 are preferably concealed by a tube compression assembly 101. The tube compression assembly 101 is received on the tube section 59 of the rod assembly 55. As best seen in FIG. 5, the tube compression assembly 101 facilitates placing the tube section 59 in fluid communication with a fitting, detector, column or conduit, generally designated by the numeral 103. The tube compression assembly 101 is made of rigid materials, such as plastic and metals.

Tube compression assembly 101 comprises a ferrule 103 and a ferrule fitting 105. The ferrule fitting 105 is rotatably slidably received on the tube section 59 extending from the compression fitting 57 to allow movement. The ferrule fitting 105 moves axially along the tube section 59 as the ferrule fitting 105 is tightened against the ferrule 103. As best seen in FIG. 5, the fitting, detector, column or conduit, generally designated by the numeral 133, has ferrule fitting receiving surfaces 109a which cooperate with threaded surfaces 109b on the ferrule fitting 105, to allow the ferrule fitting 105 to be tightened. Ferrule 103 is slidably received on tube section 59 to allow ferrule 103 to compress against a ferrule receiving surface 107 fitting, detector, column or conduit, generally designated by the numeral 133. As the ferrule fitting 105 is tightened, the ferrule 103 is sealed under compression against the tube section 59 and the ferrule receiving surface 107.

Turning now to FIGS. 1 and 4, when the device 11 is not fitted to a fitting, detector, column or conduit, generally designated by the numeral 133, an "O" ring 111 is fitted to the tube section 59 to retain the ferrule fitting 101 and the ferrule 103 in place. In use, the "O" ring 111 is removed.

The ferrule fitting 105 has a ferrule fitting interior surface 113, a ferrule fitting exterior surface 115, a ferrule fitting first opening 117 and a ferrule fitting second opening 119. The ferrule fitting interior surface 113 defines a ferrule fitting tube channel 121, as best seen in FIG. 1, between the ferrule fitting first opening 117 and the ferrule fitting second opening 119. The ferrule fitting tube channel 121 has a ferrule fitting narrow section 123a and a ferrule fitting expanded section 123b. The ferrule fitting narrow section 123a receives the tube section 59.

As best seen in FIG. 1, the ferrule fitting expanded section 123b receives and conceals the compression fitting turning surfaces 95. Thus, the user is discouraged from separating the body 13 from the compression fitting 57.

The ferrule fitting 105 has a male end 125 at the ferrule fitting second opening 119. The ferrule fitting 105 has a ferrule fitting rim 127 for receiving the ferrule 103.

Turning now to FIG. 5, the second body end 33, the body 13 has second end attachment means for affixing, in fluid communication to an analytical column, fitting, detector or a conduit, generally designated by the numeral 131. Those skilled in the art will recognize that the device 11 may accommodate flow in either direction and the use of the terms "analytical column, fitting, detector or a conduit" is intended to encompass the use of the device 11 with a flow in either direction.

Turning again to FIG. 1, second end attachment means comprise connection section 39d of passage 37. Connection section 39d has threads 141 for receiving cooperating threads of a column, or a detector or conduit, or a further fitting, generally designated by the numeral 131. Such cooperating threads are common in ferrule compression fittings and the like. For guard column applications, the total volume, from the narrows of passage 21 at end 31 to the end of tube 59 is approximately 20 to 22 microliters of which 9 to 10 microliters are occupied by a particulate bed 15 for a total device volume of approximately 10 to 12 microliters.

A further embodiment of the present invention comprises a method of separating compounds in a solution from each other or undesired components of the solution. The method comprises the step of providing a device 11 having a body 13, a separation media 15, and at least one frit element 17a or 17b as previously described. The method comprises the further step of flowing solutions through the device 11 to separate compounds from each other or from particulates.

Referring now to FIG. 5, a further embodiment of the present invention comprises an apparatus, generally designated by the numeral 151. The apparatus 151 comprises a device 11 as previously described and one or more instruments selected from the group comprising a high performance chromatography pump, detector and column, generally designated by the numerals 103 or 131.

Thus, embodiments of the present invention have been describe with respect to preferred configurations and steps with the understanding that the invention can be modified and altered without departing from the teaching herein. Thus, the present invention should not be limited to the precise details herein but should encompass the subject matter of the claims that follow and their equivalents.

The invention claimed is:

1. A device for separating compounds in a solution from each other or undesired components of the solution, said device comprising:
   a. a body having an interior surface, an exterior surface a first opening and a second opening, said first opening and said second opening defining a boundary between said interior surface and said exterior surface, said interior surface having at least one wall creating a passage in said body, said passage having at least one frit section and a media chamber proximal to said first opening and a manifold section proximal to said second opening, said at least one frit section for holding a frit, said media chamber for holding a media and said manifold section for receiving or discharging fluid from said frit section; said exterior surface having a first union means and at least one of the exterior surface and interior surface has a second union means; said first union means towards said first opening for placing said media chamber in fluid communication with at least one of a source of fluid, fluid discharge conduit, column and detector; and said second union means towards said second opening for placing said manifold section in communication at least one of the group consisting of a source of fluid, discharge conduit, column and detector; said first attachment means positioned radially about said media chamber and said at least frit section;
   b. a separation media held within said media chamber for effecting separations of compounds in solutions flowing therethrough;
   c. a frit element held in said at least one frit section for retaining said separation media; said body receiving a first conduit attachment means and a second attachment means to place said passage in fluid communication with a solution containing at least one compound to effect separation the compound from at least one of the group selected from other compounds in the solution or undesired components of the solution.

2. The device of claim 1 wherein said at least one frit element comprises a first frit element received in said frit section and a second frit element, said second frit received at or about said first end.

3. The device of claim 2 wherein said passage has a second frit section.

4. The device of claim 2 wherein exterior surface has a rim extending around said first opening for receiving a frit disc and said second frit element is a frit disc.

5. The device of claim 4 wherein said rim has a planar rim surface and at least one rim ridge surrounding said first opening, and said frit disc has a planar disc surface for receiving said rim ridge and sealing said frit disc upon compression against said rim.

6. The device of claim 5 further comprising a first union means fitted to said frit disc, said first union means for attachment to a conduit for removing fluid or placing fluid from the frit disc, fitting to a column, or fitting to a detector.

7. The device of claim 6 wherein said first union means comprises a rod assembly and compression fitting said rod assembly having tube section and a compression plate section, said tube section in fluid communication with said frit disc and said plate section having a first planar surface for pressing in sealing relationship to said frit disc and a second surface for receiving a compression surface of a compression fitting, said compression fitting received on said first attachment means of said body for compressing said plate section and frit disc against said rim.

8. The device of claim 7 wherein said first compression fitting having an fitting interior surface and a fitting exterior surface, a first end and a second end, said fitting interior surface defining a tube channel having a first opening at said first end and a second opening at said second end, said tube channel a narrow section, an expanded section and a compression surface, said compression surface interposed between said narrow section and said expanded section, said expanded section and said attachment means having cooperating threads to allow said compression surface to compress said plate section and frit disc on said rim with said tube section extending from said tube channel.

9. The device of claim 8 wherein said compression fitting has a said first end and receiving said rod assembly with said and first end and a second end, said tube channel for receiving said rod and said first attachment means have cooperating threads.

10. The device of claim 9 wherein said fitting exterior surface has turning surfaces.

11. The device of claim 10 wherein said turning surfaces are recessed.

12. The device of claim 11 further comprising a tube compression assembly.

13. The device of claim 12 wherein said tube compression assembly comprises a ferrule and a ferrule fitting.

14. The device of claim 13 wherein said ferrule fitting is received on said tube extending from said compression fitting.

15. The device of claim 14 wherein said ferrule fitting has a ferrule fitting interior surface and a ferrule fitting exterior surface and a first end and a second end, said ferrule fitting interior surface defining a ferrule fitting tube channel having a ferrule fitting narrow section and a ferrule fitting expanded section said ferrule fitting narrow section for receiving said tube section and said ferrule fitting expanded section received over said compression fitting turning surfaces to conceal said turning surfaces.

16. The device of claim 15 wherein said ferrule fitting tube channel has a ferrule fitting opening at said first end and said opening defines a rim defining the boundary of said ferrule fitting exterior surface and said ferrule fitting interior surface, said rim forming a rim compression surface receiving said ferrule to allow said ferrule to be compressed by a ferrule female fitting.

17. The device of claim 16 wherein said ferrule fitting has ferrule female fitting attachment means.

18. The device of claim 17 wherein said ferrule female fitting and said ferrule female fitting attachment means are cooperating threads.

19. The device of claim 2 wherein said compression element is compelled into the particles to form an interstitial volume fraction of approximately 0.38 to 0.35.

20. The device of claim 19 wherein said interstitial volume fraction is approximately 0.365 to 0.375.

21. The device of claim 2 wherein said compression element is compelled into the particles to effect a reduction of interstitial volume fraction from an at-rest volume of approximately 5 to 15%.

22. The device of claim 21 wherein said reduction is about 8 to 12%.

23. The device of claim 2 wherein said second frit element comprises a frit sealing ring and a second frit said second frit held in an opening in said frit sealing ring.

24. The device of claim 23 wherein said second frit has a frit thickness and second frit sealing ring has a sealing ring thickness and said frit thickness exceeds said sealing ring thicknesses to project outside the frit seal ring opening to form a second frit projection.

25. The device of claim 23 wherein said second frit projection occupies a space of 2% of the volume of the particles that occupy said chamber at rest.

26. The device of claim 2 further comprising a wiper and said chamber has a wiper recess, said wiper comprising a resilient ring and received in said recess to facilitate forming and maintaining a compressed bed of particles.

27. The device of claim 1 wherein said body second end has second end attachment means for affixing in fluid communication to an analytical column or a conduit.

28. The device of claim 27 wherein said second end attachment means are cooperating threads for receiving cooperating threads of a column.

29. The device of claim 27 wherein said second end attachment means are cooperating threads for receiving cooperating threads of a conduit fitting.

30. The device of claim 1 further comprising a compression element, said compression element compelled into the media held in said chamber to occupy approximately 0.1 to 5% of the total volume occupied by particles not under pressure.

31. The device of claim 30 wherein said compression element is forced into the at-rest particles to occupy approximately 2% of the volume.

* * * * *